US008178711B2

(12) United States Patent
Ritter

(10) Patent No.: US 8,178,711 B2
(45) Date of Patent: *May 15, 2012

(54) METHOD FOR THE PURIFICATION OF TRIORGANOPHOSPHITES BY TREATMENT WITH A BASIC ADDITIVE

(75) Inventor: Joachim C. Ritter, Wilmington, DE (US)

(73) Assignee: Invista North America S.A R.L., Wilmington, DE (US)

( * ) Notice: Subject to any disclaimer, the term of this patent is extended or adjusted under 35 U.S.C. 154(b) by 237 days.

This patent is subject to a terminal disclaimer.

(21) Appl. No.: 12/608,044

(22) Filed: Oct. 29, 2009

(65) Prior Publication Data
US 2010/0076212 A1 Mar. 25, 2010

Related U.S. Application Data

(62) Division of application No. 11/716,133, filed on Mar. 9, 2007, now Pat. No. 7,629,484.

(51) Int. Cl.
C07F 9/02 (2006.01)
(52) U.S. Cl. ........................................ 558/146
(58) Field of Classification Search ........... 558/146
See application file for complete search history.

(56) References Cited

U.S. PATENT DOCUMENTS

| | | |
|---|---|---|
| 2,768,132 A | 10/1956 | Halliwell |
| 3,370,082 A | 2/1968 | Eisfeld et al. |
| 3,496,215 A | 2/1970 | Drinkard et al. |
| 3,496,217 A | 2/1970 | Drinkard, Jr. et al. |
| 3,496,218 A | 2/1970 | Drinkard, Jr. |
| 3,522,288 A | 7/1970 | Drinkard, Jr. et al. |
| 3,536,748 A | 10/1970 | Drinkard, Jr. et al. |
| 3,551,474 A | 12/1970 | Drinkard et al. |
| 3,553,298 A | 1/1971 | Hodan et al. |
| 3,564,040 A | 2/1971 | Downing et al. |
| 3,579,560 A | 5/1971 | Drinkard et al. |
| 3,655,723 A | 4/1972 | Drinkard, Jr. et al. |
| 3,694,485 A | 9/1972 | Drinkard, Jr. et al. |
| 3,752,839 A | 8/1973 | Drinkard, Jr. et al. |
| 3,766,231 A | 10/1973 | Gosser et al. |
| 3,766,237 A | 10/1973 | Chia et al. |
| 3,766,241 A | 10/1973 | Drinkard, Jr. et al. |
| 3,773,809 A | 11/1973 | Walter |
| 3,775,461 A | 11/1973 | Drinkard, Jr. et al. |
| 3,798,256 A | 3/1974 | King et al. |
| 3,818,067 A | 6/1974 | Downing et al. |
| 3,818,068 A | 6/1974 | Wells |
| 3,846,474 A | 11/1974 | Mok |
| 3,849,472 A | 11/1974 | Waddan |
| 3,850,973 A | 11/1974 | Seidel et al. |
| 3,853,754 A | 12/1974 | Gosser |
| 3,853,948 A | 12/1974 | Drinkard, Jr. et al. |
| 3,864,380 A | 2/1975 | King et al. |
| 3,869,501 A | 3/1975 | Waddan |
| 3,920,721 A | 11/1975 | Gosser |
| 3,927,056 A | 12/1975 | Gosser |
| 3,947,487 A | 3/1976 | Crooks |
| 4,045,495 A | 8/1977 | Nazarenko et al. |
| 4,046,815 A | 9/1977 | Nazarenko |
| 4,076,756 A | 2/1978 | Nazarenko et al. |
| 4,087,452 A | 5/1978 | Kuntz |
| 4,146,555 A | 3/1979 | Kershaw |
| 4,147,717 A | 4/1979 | Kershaw |
| 4,177,215 A | 12/1979 | Seidel |
| 4,210,558 A | 7/1980 | Crooks |
| 4,230,634 A | 10/1980 | Benzie et al. |
| 4,240,976 A | 12/1980 | Benzie et al. |
| 4,251,468 A | 2/1981 | Nazarenko |
| 4,328,172 A | 5/1982 | Rapoport |
| 4,330,483 A | 5/1982 | Rapoport |
| 4,339,395 A | 7/1982 | Barnette et al. |
| 4,371,474 A | 2/1983 | Rapoport |
| 4,382,038 A | 5/1983 | McGill |
| 4,385,007 A | 5/1983 | Shook, Jr. |
| 4,416,824 A | 11/1983 | Reimer et al. |
| 4,416,825 A | 11/1983 | Ostermaier |
| 4,434,316 A | 2/1984 | Barnette |
| 4,539,302 A | 9/1985 | Leyendecker et al. |
| 4,705,881 A | 11/1987 | Rapoport |
| 4,749,801 A | 6/1988 | Bealty et al. |
| 4,774,353 A | 9/1988 | Hall et al. |
| 4,874,884 A | 10/1989 | McKinney et al. |
| 4,990,645 A | 2/1991 | Back et al. |
| 5,107,012 A | 4/1992 | Grunewald |
| 5,302,756 A | 4/1994 | McKinney |
| 5,312,959 A | 5/1994 | Sieja et al. |
| 5,449,807 A | 9/1995 | Druliner |
| 5,488,129 A | 1/1996 | Huser et al. |
| 5,512,695 A | 4/1996 | Kreutzer et al. |
| 5,512,696 A | 4/1996 | Kreutzer et al. |
| 5,523,453 A | 6/1996 | Breikss |
| 5,543,536 A | 8/1996 | Tam |
| 5,663,369 A | 9/1997 | Kreutzer et al. |
| 5,688,986 A | 11/1997 | Tam et al. |
| 5,696,280 A | 12/1997 | Shapiro |
| 5,709,841 A | 1/1998 | Reimer |
| 5,723,641 A | 3/1998 | Tam et al. |

(Continued)

FOREIGN PATENT DOCUMENTS

AU 6522096 2/1997

(Continued)

OTHER PUBLICATIONS

Houben-Weyl, Bd. XXII/2, pp. 12-17, G. Thieme Verlag, Stuttgart 1964, and supplement E1, pp. 413-421, Stuttgart, New York 1982.

(Continued)

Primary Examiner — Rei-tsang Shiao

(57) ABSTRACT

One or more triorganophosphite components are separated from a crude phosphite mixture containing acidic hydrolysis products. The crude phosphite mixture is contacted with a basic additive to produce a second mixture comprising a first phase and a second phase. The first phase comprises the basic additive and one or more acidic hydrolysis products and the second phase comprises one or more triorganophosphite components.

3 Claims, 1 Drawing Sheet

U.S. PATENT DOCUMENTS

| | | | |
|---|---|---|---|
| 5,773,637 A | 6/1998 | Cicha et al. |
| 5,821,378 A | 10/1998 | Foo et al. |
| 5,847,191 A | 12/1998 | Bunel et al. |
| 5,856,555 A | 1/1999 | Huser et al. |
| 5,908,805 A | 6/1999 | Huser et al. |
| 5,959,135 A | 9/1999 | Garner et al. |
| 6,031,120 A | 2/2000 | Tam |
| 6,069,267 A | 5/2000 | Tam |
| 6,090,987 A | 7/2000 | Billig et al. |
| 6,121,184 A | 9/2000 | Druliner et al. |
| 6,147,247 A | 11/2000 | Voit et al. |
| 6,169,198 B1 | 1/2001 | Fischer et al. |
| 6,171,996 B1 | 1/2001 | Garner et al. |
| 6,197,992 B1 | 3/2001 | Fischer et al. |
| 6,242,633 B1 | 6/2001 | Fischer et al. |
| 6,284,865 B1 | 9/2001 | Tam et al. |
| 6,307,109 B1 | 10/2001 | Kanel et al. |
| 6,355,833 B2 | 3/2002 | Fischer et al. |
| 6,461,481 B1 | 10/2002 | Barnette et al. |
| 6,469,194 B2 | 10/2002 | Burattin et al. |
| 6,521,778 B1 | 2/2003 | Fischer et al. |
| 6,646,148 B1 | 11/2003 | Kreutzer |
| 6,660,877 B2 | 12/2003 | Lenges et al. |
| 6,737,539 B2 | 5/2004 | Lenges et al. |
| 6,753,440 B2 | 6/2004 | Druliner et al. |
| 6,770,770 B1 | 8/2004 | Baumann et al. |
| 6,844,289 B2 | 1/2005 | Jackson et al. |
| 6,846,945 B2 | 1/2005 | Lenges et al. |
| 6,852,199 B2 | 2/2005 | Jungkamp et al. |
| 6,855,799 B2 | 2/2005 | Tam et al. |
| 6,897,329 B2 | 5/2005 | Jackson et al. |
| 6,984,604 B2 | 1/2006 | Cobb et al. |
| 7,022,866 B2 | 4/2006 | Bartsch et al. |
| 7,067,685 B2 | 6/2006 | Bartsch et al. |
| 7,084,293 B2 | 8/2006 | Rosier et al. |
| 7,084,294 B2 | 8/2006 | Jungkamp et al. |
| 7,098,358 B2 | 8/2006 | Burattin et al. |
| 7,105,696 B2 | 9/2006 | Burattin et al. |
| 7,253,298 B2 | 8/2007 | Galland et al. |
| 7,345,006 B2 | 3/2008 | Bartsch et al. |
| 7,381,845 B2 | 6/2008 | Weiskopf et al. |
| 7,439,381 B2 | 10/2008 | Jungkamp et al. |
| 7,442,825 B2 | 10/2008 | Galland et al. |
| 7,470,805 B2 | 12/2008 | Rosier et al. |
| 7,521,575 B2 | 4/2009 | Bartsch et al. |
| 7,528,275 B2 | 5/2009 | Bartsch et al. |
| 7,538,240 B2 | 5/2009 | Jungkamp et al. |
| 7,541,486 B2 | 6/2009 | Scheidel et al. |
| 7,629,484 B2 * | 12/2009 | Ritter ........................... 558/146 |
| 7,700,795 B2 | 4/2010 | Haderlein et al. |
| 2003/0135014 A1 | 7/2003 | Radu et al. |
| 2003/0212298 A1 | 11/2003 | Brasse et al. |
| 2004/0063991 A1 | 4/2004 | Burattin et al. |
| 2004/0176622 A1 | 9/2004 | Bartsch et al. |
| 2004/0235648 A1 | 11/2004 | Bartsch et al. |
| 2004/0260112 A1 | 12/2004 | Basset et al. |
| 2005/0090677 A1 | 4/2005 | Bartsch et al. |
| 2005/0090678 A1 | 4/2005 | Bartsch et al. |
| 2005/0247624 A1 | 11/2005 | Jungkamp et al. |
| 2006/0142609 A1 | 6/2006 | Bourgeois et al. |
| 2006/0175189 A1 | 8/2006 | Gerber et al. |
| 2006/0252955 A1 | 11/2006 | Rosier et al. |
| 2006/0258873 A1 | 11/2006 | Rosier et al. |
| 2006/0258874 A1 | 11/2006 | Bartsch et al. |
| 2006/0264651 A1 | 11/2006 | Bartsch et al. |
| 2007/0060766 A1 | 3/2007 | Bartsch et al. |
| 2007/0073071 A1 | 3/2007 | Haderlein et al. |
| 2007/0083057 A1 | 4/2007 | Haderlein et al. |
| 2007/0088173 A1 | 4/2007 | Haderlein et al. |
| 2007/0112215 A1 | 5/2007 | Jungkamp et al. |
| 2007/0155977 A1 | 7/2007 | Jungkamp et al. |
| 2007/0155978 A1 | 7/2007 | Jungkamp et al. |
| 2007/0155980 A1 | 7/2007 | Scheidel et al. |
| 2008/0015378 A1 | 1/2008 | Foo et al. |
| 2008/0015380 A1 | 1/2008 | Foo et al. |
| 2008/0015381 A1 | 1/2008 | Foo et al. |
| 2008/0015382 A1 | 1/2008 | Foo et al. |
| 2008/0071105 A1 | 3/2008 | Bartsch et al. |
| 2008/0076944 A1 | 3/2008 | Bartsch et al. |
| 2008/0083607 A1 | 4/2008 | Deckert et al. |
| 2008/0221351 A1 | 9/2008 | Bartsch et al. |
| 2008/0227214 A1 | 9/2008 | Jungkamp et al. |
| 2008/0227998 A1 | 9/2008 | Scheidel et al. |
| 2008/0242883 A1 | 10/2008 | Jungkamp et al. |
| 2008/0242885 A1 | 10/2008 | Jungkamp et al. |
| 2008/0242886 A1 | 10/2008 | Bartsch et al. |
| 2008/0275266 A1 | 11/2008 | Bartsch et al. |
| 2008/0281119 A1 | 11/2008 | Scheidel et al. |
| 2008/0281120 A1 | 11/2008 | Jungkamp et al. |
| 2009/0054671 A1 | 2/2009 | Haderlein et al. |

FOREIGN PATENT DOCUMENTS

| | | |
|---|---|---|
| AU | 199665220 A | 2/1997 |
| CA | 1324613 C | 11/1993 |
| CA | 2462720 A1 | 4/2003 |
| CA | 2552862 A1 | 8/2005 |
| CN | 1113854 A | 12/1995 |
| CN | 1145531 A | 3/1997 |
| CN | 1146166 A | 3/1997 |
| CN | 1146762 A | 4/1997 |
| CN | 1159106 A | 9/1997 |
| CN | 1159799 A | 9/1997 |
| CN | 1163606 A | 10/1997 |
| CN | 1169143 A | 12/1997 |
| CN | 1173935 A | 2/1998 |
| CN | 1179147 A | 4/1998 |
| CN | 1198151 A | 11/1998 |
| CN | 1204111 A | 1/1999 |
| CN | 1206357 A | 1/1999 |
| CN | 1211931 A | 3/1999 |
| CN | 1045591 C | 10/1999 |
| CN | 1236355 A | 11/1999 |
| CN | 1047163 C | 12/1999 |
| CN | 1245489 A | 2/2000 |
| CN | 1247102 A | 3/2000 |
| CN | 1052718 C | 5/2000 |
| CN | 1265094 A | 8/2000 |
| CN | 1266424 A | 9/2000 |
| CN | 1270543 A | 10/2000 |
| CN | 1068307 C | 7/2001 |
| CN | 1304334 A | 7/2001 |
| CN | 1069310 C | 8/2001 |
| CN | 1072980 C | 10/2001 |
| CN | 1076342 C | 12/2001 |
| CN | 1327881 A | 12/2001 |
| CN | 1331843 A | 1/2002 |
| CN | 1333745 A | 1/2002 |
| CN | 1082946 C | 4/2002 |
| CN | 1344180 A | 4/2002 |
| CN | 1356335 A | 7/2002 |
| CN | 1387534 A | 12/2002 |
| CN | 1099912 C | 1/2003 |
| CN | 1390241 A | 1/2003 |
| CN | 1103613 C | 3/2003 |
| CN | 1106218 C | 4/2003 |
| CN | 1108643 C | 5/2003 |
| CN | 1427807 A | 7/2003 |
| CN | 1449400 A | 10/2003 |
| CN | 1461295 A | 12/2003 |
| CN | 1471510 A | 1/2004 |
| CN | 1141285 C | 3/2004 |
| CN | 1142224 C | 3/2004 |
| CN | 1144781 C | 4/2004 |
| CN | 1487917 A | 4/2004 |
| CN | 1152855 C | 6/2004 |
| CN | 1535179 A | 10/2004 |
| CN | 1564807 A | 1/2005 |
| CN | 1568225 A | 1/2005 |
| CN | 1568226 A | 1/2005 |
| CN | 1617892 A | 5/2005 |
| CN | 1617900 A | 5/2005 |
| CN | 1212293 C | 7/2005 |
| CN | 1639176 A | 7/2005 |
| CN | 1213051 C | 8/2005 |
| CN | 1665776 A | 9/2005 |
| CN | 1670139 A | 9/2005 |
| CN | 1674989 A | 9/2005 |

| | | | | | | |
|---|---|---|---|---|---|---|
| CN | 1675172 | A | 9/2005 | EP | 881924 B1 | 5/2001 |
| CN | 1222358 | C | 10/2005 | EP | 854858 B1 | 6/2001 |
| CN | 1732148 | A | 2/2006 | EP | 815073 B1 | 7/2001 |
| CN | 1735460 | A | 2/2006 | EP | 1144114 A3 | 9/2001 |
| CN | 1245489 | C | 3/2006 | EP | 1091804 B1 | 2/2002 |
| CN | 1740183 | A | 3/2006 | EP | 944585 B1 | 4/2002 |
| CN | 1745062 | A | 3/2006 | EP | 1000019 B1 | 2/2003 |
| CN | 1767895 | A | 5/2006 | EP | 911339 B1 | 4/2003 |
| CN | 1260009 | C | 6/2006 | EP | 1216268 B1 | 11/2003 |
| CN | 1266424 | C | 7/2006 | EP | 1350788 A3 | 11/2003 |
| CN | 1270543 | C | 8/2006 | EP | 1003607 B1 | 12/2003 |
| CN | 1274671 | C | 9/2006 | EP | 1003716 B1 | 2/2004 |
| CN | 1274699 | C | 9/2006 | EP | 1313743 B1 | 3/2004 |
| CN | 1835915 | A | 9/2006 | EP | 1414567 A1 | 5/2004 |
| CN | 1279088 | C | 10/2006 | EP | 1427695 A1 | 6/2004 |
| CN | 1847288 | A | 10/2006 | EP | 1438133 A1 | 7/2004 |
| CN | 1283620 | C | 11/2006 | EP | 1019190 B1 | 12/2004 |
| CN | 1857775 | A | 11/2006 | EP | 1140801 B1 | 2/2005 |
| CN | 1289539 | C | 12/2006 | EP | 1395547 B1 | 3/2005 |
| CN | 1293942 | C | 1/2007 | EP | 1001928 B1 | 4/2005 |
| CN | 1906150 | A | 1/2007 | EP | 1521736 A1 | 4/2005 |
| CN | 1914154 | A | 2/2007 | EP | 1521737 A1 | 4/2005 |
| CN | 1914155 | A | 2/2007 | EP | 1521738 A2 | 4/2005 |
| CN | 1914156 | A | 2/2007 | EP | 1603865 A1 | 12/2005 |
| CN | 1914157 | A | 2/2007 | EP | 1324976 B1 | 2/2006 |
| CN | 1914158 | A | 2/2007 | EP | 1214975 B1 | 3/2006 |
| CN | 1914159 | A | 2/2007 | EP | 1324978 B1 | 3/2006 |
| CN | 1914160 | A | 2/2007 | EP | 1648860 A1 | 4/2006 |
| CN | 1914161 | A | 2/2007 | EP | 891323 B1 | 6/2006 |
| CN | 1914162 | A | 2/2007 | EP | 1226147 B1 | 6/2006 |
| CN | 1914165 | A | 2/2007 | EP | 1438317 B1 | 6/2006 |
| CN | 1914166 | A | 2/2007 | EP | 1682561 A1 | 7/2006 |
| CN | 1914167 | A | 2/2007 | EP | 1448668 B1 | 8/2006 |
| CN | 1914216 | A | 2/2007 | EP | 1587621 B1 | 8/2006 |
| CN | 1307237 | C | 3/2007 | EP | 1713759 A1 | 10/2006 |
| CN | 1315790 | C | 5/2007 | EP | 1713761 A1 | 10/2006 |
| CN | 1318432 | C | 5/2007 | EP | 1713762 A1 | 10/2006 |
| CN | 1997624 | A | 7/2007 | EP | 1713766 A1 | 10/2006 |
| CN | 1331843 | C | 8/2007 | EP | 1716102 A2 | 11/2006 |
| CN | 101020641 | A | 8/2007 | EP | 1716103 A1 | 11/2006 |
| CN | 101035799 | A | 9/2007 | EP | 1716104 A1 | 11/2006 |
| CN | 101043946 | A | 9/2007 | EP | 1716105 A1 | 11/2006 |
| CN | 100348322 | C | 11/2007 | EP | 1716106 A1 | 11/2006 |
| CN | 100351227 | C | 11/2007 | EP | 1716107 A1 | 11/2006 |
| CN | 100352824 | C | 12/2007 | EP | 1716109 A2 | 11/2006 |
| CN | 100361966 | C | 1/2008 | EP | 162153 B1 | 3/2007 |
| CN | 100364666 | C | 1/2008 | EP | 1610893 B1 | 3/2007 |
| DE | 1807088 | U | 3/1960 | EP | 1438132 B1 | 4/2007 |
| DE | 1807088 | A1 | 6/1969 | EP | 1799697 A1 | 6/2007 |
| DE | 2055747 | A1 | 5/1971 | EP | 1713764 B1 | 8/2007 |
| DE | 1593277 | B2 | 8/1973 | EP | 1713816 B1 | 8/2007 |
| DE | 1593277 | C3 | 3/1974 | EP | 1825914 A1 | 8/2007 |
| DE | 2700904 | C2 | 10/1983 | EP | 1448620 B1 | 6/2008 |
| DE | 68909466 | T2 | 3/1994 | EP | 1817108 B1 | 6/2008 |
| DE | 10136488 | A1 | 2/2003 | EP | 1713760 B1 | 7/2008 |
| DE | 10150285 | A1 | 4/2003 | EP | 1571172 B1 | 10/2008 |
| DE | 10350999 | A1 | 6/2005 | EP | 1988998 A1 | 11/2008 |
| DE | 102004004696 | A1 | 8/2005 | EP | 1265832 B1 | 5/2009 |
| EP | 0001899 | B1 | 3/1982 | EP | 1592659 B1 | 7/2009 |
| EP | 123438 | B1 | 7/1987 | EP | 1586598 B1 | 9/2009 |
| EP | 160296 | B1 | 10/1988 | EP | 2098106 A1 | 9/2009 |
| EP | 268448 | B1 | 9/1991 | EP | 1567478 B1 | 10/2009 |
| EP | 510689 | A1 | 10/1992 | EP | 1682559 B1 | 12/2009 |
| EP | 248643 | B1 | 3/1993 | EP | 1630166 B1 | 2/2010 |
| EP | 336314 | B1 | 9/1993 | FR | 1544656 A | 11/1968 |
| EP | 464691 | B1 | 12/1993 | FR | 2015115 A5 | 4/1970 |
| EP | 675871 | B1 | 4/1997 | FR | 1603513 A | 5/1971 |
| EP | 634395 | B1 | 9/1997 | FR | 2069411 A5 | 9/1971 |
| EP | 650959 | B1 | 9/1997 | FR | 2845379 B1 | 12/2004 |
| EP | 784610 | B1 | 2/1999 | FR | 2873696 A1 | 2/2006 |
| EP | 757672 | B1 | 6/1999 | FR | 2873696 B1 | 10/2006 |
| EP | 792259 | B1 | 8/1999 | GB | 0219474 | 7/1924 |
| EP | 804412 | B1 | 12/1999 | GB | 1104140 A | 2/1968 |
| EP | 1000019 | A1 | 5/2000 | GB | 1203702 A | 9/1970 |
| EP | 1001928 | A1 | 5/2000 | GB | 1213175 A | 11/1970 |
| EP | 1003716 | A1 | 5/2000 | GB | 1429169 A | 3/1976 |
| EP | 1019190 | A1 | 7/2000 | GB | 1429621 A | 3/1976 |
| EP | 755302 | B1 | 10/2000 | GB | 1436932 A | 5/1976 |
| EP | 929513 | B1 | 4/2001 | GB | 1458322 A | 12/1976 |

| | | | | | | | |
|---|---|---|---|---|---|---|---|
| GB | 1482909 | A | 8/1977 | JP | 03285878 | B2 | 5/2002 |
| GB | 2007521 | A | 5/1979 | JP | 2002517473 | A | 6/2002 |
| GB | 1565443 | A | 4/1980 | JP | 03320424 | B2 | 9/2002 |
| GB | 1594694 | A | 8/1981 | JP | 2002533321 | A | 10/2002 |
| GB | 2007521 | B | 6/1982 | JP | 03380543 | B2 | 2/2003 |
| HK | 1025950 | A1 | 7/2003 | JP | 2003510385 | A | 3/2003 |
| HK | 1026383 | A1 | 7/2004 | JP | 2003526688 | A | 9/2003 |
| HK | 1052364 | A1 | 5/2007 | JP | 03478399 | B2 | 12/2003 |
| JP | 48028423 | Y1 | 8/1973 | JP | 2004501058 | A | 1/2004 |
| JP | 48028423 | B | 9/1973 | JP | 2004507550 | A | 3/2004 |
| JP | 49043924 | Y1 | 12/1974 | JP | 03519410 | B2 | 4/2004 |
| JP | 50053926 | U | 6/1975 | JP | 03535172 | B2 | 6/2004 |
| JP | 50059324 | U | 6/1975 | JP | 03553952 | B2 | 8/2004 |
| JP | 51007649 | B | 3/1976 | JP | 2004534032 | A | 11/2004 |
| JP | 52012698 | B | 4/1977 | JP | 2004535929 | A | 12/2004 |
| JP | 1013127 | C | 9/1980 | JP | 03621133 | B2 | 2/2005 |
| JP | 55047031 | B | 11/1980 | JP | 2005503410 | A | 2/2005 |
| JP | 57156454 | U | 10/1982 | JP | 2005505610 | A | 2/2005 |
| JP | 57156455 | U | 10/1982 | JP | 2005505611 | A | 2/2005 |
| JP | 57179144 | U | 11/1982 | JP | 2005510588 | A | 4/2005 |
| JP | 1136333 | C | 2/1983 | JP | 2005510605 | A | 4/2005 |
| JP | 58067658 | U | 5/1983 | JP | 2004509942X | | 10/2005 |
| JP | 58126892 | U | 8/1983 | JP | 2005533095 | A | 11/2005 |
| JP | 1170710 | C | 10/1983 | JP | 2005533096 | A | 11/2005 |
| JP | 58159452 | U | 10/1983 | JP | 2005538075 | A | 12/2005 |
| JP | 60044295 | A | 3/1985 | JP | 03739404 | B2 | 1/2006 |
| JP | 60044295 | B | 10/1985 | JP | 2004534032X | | 1/2006 |
| JP | 62294691 | A | 12/1987 | JP | 2004535929X | | 1/2006 |
| JP | 63135363 | U | 9/1988 | JP | 2006000451 | A | 1/2006 |
| JP | 1013127 | Y2 | 4/1989 | JP | 2006511591 | A | 4/2006 |
| JP | 1209830 | A | 8/1989 | JP | 2006519797 | A | 8/2006 |
| JP | 1136333 | U | 9/1989 | JP | 2006528616 | A | 12/2006 |
| JP | 1050220 | B | 10/1989 | JP | 2007083057 | A | 4/2007 |
| JP | 1173751 | U | 12/1989 | JP | 2007509885 | A | 4/2007 |
| JP | 1565159 | C | 6/1990 | JP | 2007509886 | A | 4/2007 |
| JP | 3001298 | B | 1/1991 | JP | 2007509887 | A | 4/2007 |
| JP | 1615749 | C | 8/1991 | JP | 2007519516 | A | 7/2007 |
| JP | 3205587 | A | 9/1991 | JP | 2007519663 | A | 7/2007 |
| JP | 1627124 | C | 11/1991 | JP | 2007519664 | A | 7/2007 |
| JP | 1627146 | C | 11/1991 | JP | 2007519666 | A | 7/2007 |
| JP | 3069915 | B | 11/1991 | JP | 2007519667 | A | 7/2007 |
| JP | 3285878 | A | 12/1991 | JP | 2007519670 | A | 7/2007 |
| JP | 1642102 | C | 2/1992 | JP | 2007519671 | A | 7/2007 |
| JP | 4012248 | Y2 | 3/1992 | JP | 2007519672 | A | 7/2007 |
| JP | 4057050 | U | 5/1992 | JP | 2007519673 | A | 7/2007 |
| JP | 4166155 | A | 6/1992 | JP | 2007519674 | A | 7/2007 |
| JP | 4230254 | A | 8/1992 | JP | 2007519675 | A | 7/2007 |
| JP | 4057050 | B | 9/1992 | JP | 2007519677 | A | 7/2007 |
| JP | 4060532 | B | 9/1992 | JP | 2007522122 | A | 8/2007 |
| JP | 4118676 | U | 10/1992 | JP | 04012248 | B2 | 11/2007 |
| JP | 4128141 | U | 11/1992 | JP | 2006515323X | | 2/2008 |
| JP | 1729140 | C | 1/1993 | JP | 04057050 | B2 | 3/2008 |
| JP | 1811422 | C | 12/1993 | JP | 04060532 | B2 | 3/2008 |
| JP | 7025841 | Y2 | 6/1995 | JP | 2006512918X | | 3/2008 |
| JP | 7188144 | A | 7/1995 | JP | 2008515831 | A | 5/2008 |
| JP | 2037346 | C | 3/1996 | JP | 2008516907 | A | 5/2008 |
| JP | 8504814 | A | 5/1996 | JP | 04118676 | B2 | 7/2008 |
| JP | 8157795 | A | 6/1996 | JP | 04128141 | B2 | 7/2008 |
| JP | 2098106 | C | 10/1996 | JP | 04166155 | B2 | 10/2008 |
| JP | 02521777 | Y2 | 1/1997 | JP | 04230254 | B2 | 2/2009 |
| JP | 02623448 | B2 | 6/1997 | KR | 198802621 | Y1 | 7/1988 |
| JP | 9505586 | A | 6/1997 | KR | 198802296 | B | 10/1988 |
| JP | 9512013 | A | 12/1997 | KR | 198802296 | B1 | 10/1988 |
| JP | 10505101 | A | 5/1998 | KR | 199003458 | B1 | 5/1990 |
| JP | 10506911 | A | 7/1998 | KR | 199008166 | B1 | 11/1990 |
| JP | 10509954 | A | 9/1998 | KR | 199104132 | B1 | 6/1991 |
| JP | 02818503 | B2 | 10/1998 | KR | 199205087 | Y1 | 7/1992 |
| JP | 10512879 | A | 12/1998 | KR | 2006132885 | A | 12/2006 |
| JP | 11501660 | A | 2/1999 | MX | 2004PA002764 | A | 6/2004 |
| JP | 11504262 | A | 4/1999 | NL | 197700262 | A | 7/1977 |
| JP | 02911608 | B2 | 6/1999 | NL | 188158 | C | 4/1992 |
| JP | 11507297 | A | 6/1999 | SU | 677650 | A | 7/1979 |
| JP | 03001298 | B2 | 1/2000 | TW | 387874 | B | 4/2000 |
| JP | 03069915 | B2 | 7/2000 | TW | 400249 | B | 8/2000 |
| JP | 2001500135 | A | 1/2001 | TW | 453983 | B | 9/2001 |
| JP | 2001506250 | A | 5/2001 | TW | 453985 | B | 9/2001 |
| JP | 2001512097 | A | 8/2001 | TW | 455576 | B | 9/2001 |
| JP | 03205587 | B2 | 9/2001 | TW | 457244 | B | 10/2001 |
| JP | 2001516640 | A | 10/2001 | TW | 458959 | B | 10/2001 |

| | | | |
|---|---|---|---|
| TW | 519496 B | 2/2003 |
| TW | 527340 B | 4/2003 |
| TW | 576837 B | 2/2004 |
| TW | 580489 B | 3/2004 |
| TW | 580490 B | 3/2004 |
| TW | 584623 B | 4/2004 |
| TW | 592821 B | 6/2004 |
| TW | 226345 B | 1/2005 |
| TW | 233438 B | 6/2005 |
| TW | 245780 B | 12/2005 |
| TW | 266650 B | 11/2006 |
| WO | WO7900193 A1 | 4/1979 |
| WO | WO9414752 A1 | 7/1994 |
| WO | WO9514659 A1 | 6/1995 |
| WO | WO9528228 A1 | 10/1995 |
| WO | WO9529153 A1 | 11/1995 |
| WO | WO9611182 A1 | 4/1996 |
| WO | WO9616022 A1 | 5/1996 |
| WO | WO9622968 A1 | 8/1996 |
| WO | WO9629303 A1 | 9/1996 |
| WO | WO9703040 A1 | 1/1997 |
| WO | WO9712857 A1 | 4/1997 |
| WO | WO9724183 A1 | 7/1997 |
| WO | WO9736855 A2 | 10/1997 |
| WO | WO9811051 A1 | 3/1998 |
| WO | WO9827054 A1 | 6/1998 |
| WO | WO9906146 A2 | 2/1999 |
| WO | WO9906356 | 2/1999 |
| WO | WO9906359 A1 | 2/1999 |
| WO | WO9913983 A1 | 3/1999 |
| WO | WO9964155 A1 | 12/1999 |
| WO | WO0001485 A2 | 1/2000 |
| WO | WO0037431 A1 | 6/2000 |
| WO | WO0121684 A1 | 3/2001 |
| WO | WO0136429 A1 | 5/2001 |
| WO | WO0168247 A2 | 9/2001 |
| WO | WO0211108 A1 | 2/2002 |
| WO | WO0213964 A2 | 2/2002 |
| WO | WO0218392 A1 | 3/2002 |
| WO | WO0226698 A1 | 4/2002 |
| WO | WO0230854 A2 | 4/2002 |
| WO | WO02053527 A1 | 7/2002 |
| WO | WO02092551 A2 | 11/2002 |
| WO | WO03011457 A1 | 2/2003 |
| WO | WO03018540 A1 | 3/2003 |
| WO | WO03024919 A1 | 3/2003 |
| WO | WO03031392 A1 | 4/2003 |
| WO | WO03033141 A1 | 4/2003 |
| WO | WO03033509 A1 | 4/2003 |
| WO | WO03046019 A1 | 6/2003 |
| WO | WO03046049 A1 | 6/2003 |
| WO | WO03068729 A1 | 8/2003 |
| WO | WO03076394 A1 | 9/2003 |
| WO | WO2004007431 A1 | 1/2004 |
| WO | WO2004007432 A1 | 1/2004 |
| WO | WO2004007435 A2 | 1/2004 |
| WO | WO2004007508 A2 | 1/2004 |
| WO | WO01068247 A8 | 6/2004 |
| WO | WO2004060855 A1 | 7/2004 |
| WO | WO2004064994 A2 | 8/2004 |
| WO | WO2004065352 A2 | 8/2004 |
| WO | WO2004080924 A2 | 9/2004 |
| WO | WO2004080948 A1 | 9/2004 |
| WO | WO2004087314 A1 | 10/2004 |
| WO | WO2005019160 A1 | 3/2005 |
| WO | WO2005042156 A1 | 5/2005 |
| WO | WO2005042157 A2 | 5/2005 |
| WO | WO2005042547 A1 | 5/2005 |
| WO | WO2005042549 A1 | 5/2005 |
| WO | WO2005073167 A1 | 8/2005 |
| WO | WO2005073168 A1 | 8/2005 |
| WO | WO2005073169 A1 | 8/2005 |
| WO | WO2005073170 A1 | 8/2005 |
| WO | WO2005073171 A1 | 8/2005 |
| WO | WO2005073172 A1 | 8/2005 |
| WO | WO2005073173 A1 | 8/2005 |
| WO | WO2005073174 A1 | 8/2005 |
| WO | WO2005073175 A1 | 8/2005 |
| WO | WO2005073176 A1 | 8/2005 |
| WO | WO2005073178 A2 | 8/2005 |
| WO | WO2005073179 A1 | 8/2005 |
| WO | WO2005073241 A1 | 8/2005 |
| WO | WO2006040023 A1 | 4/2006 |
| WO | WO2006042675 A2 | 4/2006 |
| WO | WO2005073166 A3 | 3/2007 |
| WO | WO2007051374 A1 | 5/2007 |
| WO | WO2007096274 A1 | 8/2007 |
| WO | 2007115936 | 10/2007 |
| WO | WO2007115936 A2 | 10/2007 |
| WO | WO2008008926 A2 | 1/2008 |
| WO | WO2008008928 A2 | 1/2008 |
| WO | WO2008008929 A2 | 1/2008 |
| WO | WO2008008930 A2 | 1/2008 |
| WO | WO2008028843 A1 | 3/2008 |
| WO | WO2008062058 A1 | 5/2008 |

OTHER PUBLICATIONS

Houben-Weyl, Bd. XXII/2, pp. 30-32, G. Thieme Verlag, Stuttgart 1964.
Gerard, Hudson and Healy in G. M. Kosolapoff & L. Maier Eds., Organic Phosphorus Compounds, vol. 5, pp. 41-42, Wiley & Sons, New York 1973.
Healy et al., J. Inorg. Nucl. Chem., 1974, 36, pp. 2579-2583.
Westheimer et al., J. Amer. Chem. Soc., 1988, 110, pp. 181-185.

\* cited by examiner

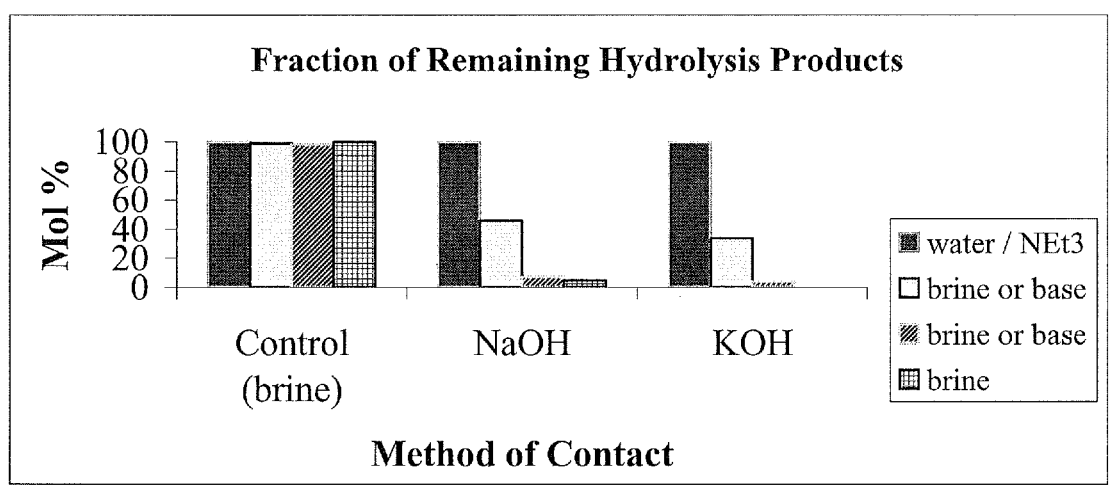

US 8,178,711 B2

METHOD FOR THE PURIFICATION OF TRIORGANOPHOSPHITES BY TREATMENT WITH A BASIC ADDITIVE

CROSS-REFERENCE TO RELATED APPLICATIONS

This Divisional application claims benefit of priority from application Ser. No. 11/716,133, filed Mar. 9, 2007. This Divisional application hereby incorporates by reference application Ser. No. 11/716,133 in its entirety.

FIELD OF THE INVENTION

The invention relates to the field of preparation and use of triorganophosphite compounds. More specifically, the invention relates to the partial removal of phosphorus acids in triorganophosphite product streams by treatment with a basic additive. Because the phosphorus acids can act as catalysts for triorganophosphite hydrolysis, the treated triorganophosphite product streams can be stabilized against further hydrolysis when exposed to water.

BACKGROUND OF THE INVENTION

Triorganophosphites of the general structure $(R^4O)(R^5O)P(OR^6)$ and $((R^7O)(R^8O)PO)_nA$, where "A" is an optionally substituted or unsubstituted aliphatic, aromatic, or heteroaromatic radical and n is an integer greater than 1, are used in a number of important commercial applications including their use as antioxidants, stabilizers, anti-wear additives and as ligands for various catalytic processes. Generally, triorganophosphites are produced from $PX_3$ (X=Cl, Br, or I) and the corresponding alcohols (ROH). This reaction occurs stepwise by displacement of X with OR. When X is Cl, the process can form phosphorodichloridite $(R^4O)PCl_2$ and phosphorochloridite $(R^4O)(R^5O)PCl$ intermediates, triorganophosphites $(R^4O)(R^5O)P(OR^6)$ and acid HX.

Several methods for making organophosphites, for example those described in Houben-Weyl, Bd. XXII/2 pages 12-17, G. Thieme Verlag, Stuttgart 1964, and supplement E1, pages 413-421 Stuttgart, N.Y. 1982, are known using readily available $PCl_3$ and the corresponding alcohols. The acid HX can be removed by physical separation or by acid-base reaction using organic or inorganic bases. In addition, U.S. Pat. No. 6,069,267, and U.S. Pat. No. 6,031,120 describe the use of triorganoamines to remove HCl followed by water washing at low temperatures to remove the corresponding ammonium hydrochloride salts from the triorganophosphite mixture.

Houben-Weyl, Bd. XXII/2 Chapter I and pages 30-32, G. Thieme Verlag, Stuttgart 1964 teaches that triorganophosphites are easily hydrolyzed in the presence of water, especially in the presence of acidic compounds, to produce one or more of the compounds diorganohydrogenphosphite $(R^2O)(R^3O)POH$, organodihydrogenphosphite $(R^1O)(HO)PO(H)$, and phosphorous acid $H_3PO_3$. Gerard, Hudson and Healy, respectively, (in G. M. Kosolapoff & L. Maier Eds., Organic Phosphorous Compounds, Vol. 5 pages 41-42, Wiley & Sons., New York, 1973; Healy et al. J. Inorg. Nucl. Chem., 1974, 36, 2579) teach that this hydrolysis reaction is autocatalytic due to the acidic properties of diorganohydrogenphosphite $(R^2O)(R^3O)POH$, organodihydrogenphosphite $(R^1O)(OH)PO(H)$ and $H_3PO_3$. Hydrolysis under basic conditions was found to be slower than hydrolysis in the presence of acids (Westheimer et al., J. Amer. Chem. Soc. 1988, 110, 183). Without the removal of these acidic hydrolysis products, as a result of hydrolysis, there can be significant degradation and loss of the triorganophosphite product during downstream processing and storage. In order to at least partially address this effect, U.S. Pat. No. 3,553,298 teaches that nitrogen-containing compound additives such as amines and magnesium oxide can partially stabilize the triorganophosphites by retarding hydrolysis. However, such additives can cause undesirable effects or be incompatible with the use of the triorganophosphites, for example during preparation of a transition metal-triorganophosphite catalyst or catalyst precursor for reactions such as hydrocyanation and hydroformylation, for example. It would, therefore, be desirable to have a method to stabilize triorganophosphites without using additives that may provide undesirable side effects.

U.S. Pat. No. 6,069,267 Example 1 discloses a sequential treatment of a triorganophosphite reaction mixture in an organic solvent with 0.1 N aqueous HCl, 0.1 N aqueous NaOH, followed by distilled water.

U.S. Pat. No. 6,844,289 discloses a process for combining a crude ligand mixture, prepared for example by the process of U.S. Pat. No. 6,069,267, with divalent nickel compounds and reducing agents to produce a catalyst which is a complex of nickel and a bidentate phosphorus compound. This patent discloses that such crude ligand mixture can contain byproducts which may affect the rate of formation of the nickel-containing catalyst. Disclosed therein are treatment methods which include contacting crude ligand mixture with one or more of, for example, a weakly basic organic resin and a two phase solvent system for liquid-liquid extraction. The patent discloses that various treatments of crude ligand may overcome deleterious rate inhibiting effects of byproduct impurities which are present in the crude ligand.

SUMMARY OF THE INVENTION

As described above, triorganophosphites can be hydrolyzed in basic as well as acidic conditions, with base-catalyzed hydrolysis being slower than acid-catalyzed hydrolysis. In this regard, it has been discovered that hydrolysis products can be removed by treatment with a strong base, so that the overall degradation of triorganophosphite may be decreased.

The present invention includes a method for separating one or more triorganophosphite components from a crude phosphite mixture containing acidic hydrolysis products by contacting the crude phosphite mixture with a basic additive to produce a second mixture comprising a first phase and a second phase. The first phase comprises the basic additive and one or more components independently selected from the group consisting of $(R^2O)(R^3O)POH$, $(R^1O)(HO)PO(H)$ and $H_3PO_3$ wherein $R^1$, $R^2$ and $R^3$ are independently selected from the group consisting of $C_1$ to $C_{18}$ alkyl, $C_6$ to $C_{18}$ aryl and hydroxyaryl, and $C_3$ to $C_{18}$ cycloalkyl and hydroxyalkyl radicals, and wherein $R^2$ and $R^3$ can optionally be connected to each other directly by a chemical bond or through an intermediate divalent group $R^9$. $R^9$ is selected from the group consisting —O—, —S—, and —CH($R^{12}$)—, wherein $R^{12}$ is selected from the group comprising H, $C_6$ to $C_{18}$ aryl, and $C_1$ to $C_{18}$ alkyl.

The second phase comprises one or more triorganophosphite components independently selected from the group consisting of $(R^4O)(R^5O)P(OR^6)$ and $((R^7O)(R^8O)PO)_nA$, wherein $R^4$, $R^5$, $R^6$, $R^7$ and $R^8$ are independently selected from the group consisting of $C_1$ to $C_{18}$ alkyl, $C_6$ to $C_{18}$ aryl and $C_3$ to $C_{18}$ cycloalkyl radicals, and wherein each $R^4$, $R^5$ and $R^6$ can optionally be connected to one or both of the other two directly by a chemical bond or through an intermediate divalent group $R^{10}$, and $R^7$ and $R^8$ can optionally be connected to each other directly by a chemical bond or through an intermediate divalent group $R^{11}$. The intermediate divalent groups $R^{10}$ and $R^{11}$ are independently selected from the group consisting of —O—, —S—, and —CH($R^{12}$)—, wherein $R^{12}$ is selected from the group consisting of H, $C_6$ to $C_{18}$ aryl, and $C_1$ to $C_{18}$ alkyl. The substituent "A" is an optionally substituted or unsubstituted aliphatic, aromatic, or heteroaromatic radical and n is an integer greater than 1. Examples of A include $C_1$ to $C_{18}$ aliphatic, $C_6$ to $C_{28}$ aromatic, or $C_3$ to $C_{28}$ heteroaromatic radicals.

The basic additive can comprise at least one compound selected from the group consisting of NaOH, KOH, $Na_2CO_3$, $K_2CO_3$, $Ca(OH)_2$, $NH_4OH$, $CaCO_3$, a strongly basic anion-exchange resin, and combinations thereof. In one embodiment, the basic additive comprises a strongly basic anion-exchange resin, for example a strongly basic anion-exchange resin comprising polymer-bound tetraorgano-ammonium hydroxide groups.

In one embodiment of the present invention, the basic additive and the crude phosphite mixture are contacted at temperatures above about −25° C., for example at temperatures from about −10° C. to about 30° C.

In yet another embodiment of the present invention, the first phase is maintained at or above a pH of about 13.5 throughout the contacting process.

The present invention also relates to a method for separating triorganophosphite components from a crude phosphite mixture containing acidic hydrolysis products which further comprises the step of contacting the crude phosphite mixture with water before contacting the crude phosphite mixture with the basic additive.

The present invention also relates to methods for separating triorganophosphite components from a crude phosphite mixture containing acidic hydrolysis products wherein the methods further comprise the steps of separating the first phase from the second phase, and contacting the second phase with the basic additive. In another embodiment the present invention includes contacting the second phase with a brine solution after contacting with the basic additive.

Another embodiment of the present invention further comprises contacting the second phase with a transition metal or a transition metal compound to produce a transition metal-triorganophosphite catalyst or catalyst precursor. Examples of transition metals or transition metal compounds that can be used include Ni(COD)$_2$ (COD is 1,5-cyclooctadiene), Ni[P(O-o-$C_6H_4CH_3$)$_3$]$_3$ and Ni[P(O-o-$C_6H_4CH_3$)$_3$]$_2$($C_2H_4$), all of which are known in the art. The resulting transition metal-triorganophosphite catalyst or catalyst precursor can be useful for reactions such as hydrocyanation or hydroformylation, for example.

The invention also relates to a method for preparing triorganophosphites, which comprises contacting an alcohol with $PCl_3$ in the presence of a triorganoamine to produce a first reaction product comprising one or more organophosphites and triorganoamine hydrochloride; removing the triorganoamine hydrochloride from the first reaction product to produce a second reaction product optionally containing one or more triorganophosphites, diorganohydrogenphosphite ($R^2O$)($R^3O$)POH, organodihydrogenphosphite ($R^1O$)(HO)PO(H) and $H_3PO_3$, wherein $R^1$, $R^2$ and $R^3$ are independently selected from the group consisting of $C_1$ to $C_{18}$ alkyl, $C_6$ to $C_{18}$ aryl and hydroxyaryl, and $C_3$ to $C_{18}$ cycloalkyl and hydroxyalkyl radicals, and wherein $R^2$ and $R^3$ can optionally be connected to each other directly by a chemical bond or through an intermediate divalent group $R^9$, wherein $R^9$ is selected from the group consisting of —O—, —S—, and —CH($R^{12}$)—, wherein $R^{12}$ is selected from the group consisting of H, $C_6$ to $C_{18}$ aryl, and $C_1$ to $C_{18}$ alkyl; and removing at least a portion of one or more of the compounds diorganohydrogenphosphite ($R^2O$)($R^3O$)POH, organodihydrogenphosphite ($R^1O$)(HO)PO(H) and $H_3PO_3$ by contacting the second reaction product with a basic additive.

BRIEF DESCRIPTION OF THE FIGURE

FIG. 1 is a graphical representation showing the fraction of hydrolysis products remaining in the organic phase after contact with a control (brine) as compared to contact with a basic additive.

DETAILED DESCRIPTION OF THE INVENTION

The present invention includes methods for purifying and stabilizing triorganophosphites by removing acidic impurities from the phase containing the triorganophosphites. For example, acidic impurities such as diorganohydrogenphosphite ($R^2O$)($R^3O$)POH, organodihydrogenphosphite ($R^1O$)(HO)PO(H), and $H_3PO_3$ can occur as a result of aqueous workup of crude triorganophosphites, such as ($R^4O$)($R^5O$)P($OR^6$), and (($R^7O$)($R^8O$)PO)$_n$A, and from unconverted phosphorodichloridite ($R^4O$)PCl$_2$ and phosphorochloridite ($R^4O$)($R^5O$)PCl intermediates used as components for the making of triorganophosphites. Furthermore, small amounts of the above-described acidic impurities can increase in concentration during storage of triorganophosphite materials by autocatalytic hydrolysis upon exposure to moisture, causing yield loss and undesirable effects with the use of triorganophosphites in applications such as catalysis. At least one of these disadvantages may be overcome by removal of acidic impurities by means of extraction with a basic additive.

In at least one embodiment falling within the scope of the present invention, a crude phosphite mixture comprising at least one triorganophosphite selected from the group consisting of ($R^4O$)($R^5O$)P($OR^6$), and (($R^7O$)($R^8O$)PO)$_n$A; and one or more of the compounds diorganohydrogenphosphite ($R^2O$)($R^3O$)POH, organodihydrogenphosphite ($R^1O$)(HO)PO(H), and $H_3PO_3$ is contacted with a basic additive to produce a second mixture. The second mixture comprises two phases—a first phase and a second phase. The first phase comprises the basic additive and at least a portion of one or more of the components consisting of diorganohydrogenphosphite ($R^2O$)($R^3O$)POH, organodihydrogenphosphite ($R^1O$)(HO)PO(H), and $H_3PO_3$. The second phase comprises at least a portion of the organophosphites. The first phase of the second mixture can optionally be separated from the second phase, using general separation methods known by those skilled in the art. For example, if the basic phase is liquid, such as aqueous NaOH, a conventional mixer-settler can be used to contact the crude phosphite mixture and aqueous NaOH then separate the second phase comprising the triorganophosphites from the first phase comprising the acidic impurities. If, instead, a basic ion-exchange resin is deployed, a decanter or filter may be used.

$R^1$, $R^2$, and $R^3$ are independently selected from the group consisting of $C_1$ to $C_{18}$ alkyl, $C_6$ to $C_{18}$ aryl and hydroxyaryl, and $C_3$ to $C_{18}$ cycloalkyl and hydroxyalkyl radicals; $R^2$ and $R^3$ can optionally be connected to each other directly by a chemical bond or through an intermediate divalent group $R^9$. $R^9$ is selected from the group consisting of —O—, —S—, and —CH($R^{12}$)—, wherein $R^{12}$ is selected from the group consisting of H, $C_6$ to $C_{18}$ aryl, or $C_1$ to $C_{18}$ alkyl.

$R^4$, $R^5$, $R^6$, $R^7$, and $R^8$ are independently selected from the group consisting of $C_1$ to $C_{18}$ alkyl, $C_6$ to $C_{18}$ aryl, and $C_3$ to $C_{18}$ cycloalkyl radicals. Each of $R^4$, $R^5$, and $R^6$ can optionally be connected to one or both of the other two directly by a chemical bond or through an intermediate divalent group $R^{10}$. $R^7$ and $R^8$ can optionally be connected to each other directly by a chemical bond or through an intermediate divalent group $R^{11}$. $R^{10}$ and $R^{11}$ are independently selected from the group consisting of —O—, —S—, and —CH($R^{12}$)—, wherein $R^{12}$ is selected from the group consisting of H, $C_6$ to $C_{18}$ aryl, and $C_1$ to $C_{18}$ alkyl. The substituent "A" is an optionally substituted or unsubstituted aliphatic, aromatic or heteroaromatic radical where n is an integer greater than 1.

The basic additive employed in the present invention can comprise one or more compositions comprising at least one basic compound and/or material. The basic additive may, for example, comprise at least one compound selected from the group consisting of NaOH, KOH, $Na_2CO_3$, $K_2CO_3$, $Ca(OH)_2$, $NH_4OH$, $CaCO_3$, a strongly basic anion-exchange resin, and combinations thereof. Examples of suitable strongly basic ion-exchange resins are resins comprising polymer-bound tetraorgano-ammonium hydroxide groups.

Since hydrolysis rates are dependent on temperature, the extraction temperature should ideally be as low as possible only restricted by physical limits. In the case of liquid-liquid extractions, a physical limit impacting the range of suitable operation temperatures is, for example, the freezing point of the liquid phases. Since under commercial operation the temperature range achievable is subject to the limits of the equipment available, temperatures above about −25° C. are generally preferred. An example of a non-limiting temperature range for this process is from about ±10° C. to about 30° C.

Ideally, the pH of the basic phase should remain at or above about 13.5 throughout the extraction process. This can be accomplished by using a 1 normal solution of a strong base in water or a strongly basic anion-exchange resin of equivalent strength. If the production of the triorganophosphite generates a salt constituting a weak acid such as a triorganoamine hydrochloride, the weak acid should be removed first to allow for an effective extraction process of the acidic diorganohydrogenphosphite ($R^2$O)($R^3$O)POH, organodihydrogenphosphite ($R^1$O)(HO)PO(H), and $H_3PO_3$ impurities with the basic additive. Triorganoamine hydrochloride salt removal can be achieved by filtration and/or by water extraction prior to contacting with the basic additive as, for example, described in U.S. Pat. Nos. 6,069,267, and 6,031,120.

The total amount of molar equivalents of base to be used is, at least in part, a function of the total amount of molar equivalents of acidic diorganohydrogenphosphite ($R^2$O)($R^3$O) POH, organodihydrogenphosphite ($R^1$O)(HO)PO(H), and $H_3PO_3$ impurities that are present prior to the treatment with the basic additive. For example, a 10- to 1000-fold excess of the base can be suitable, provided that, in the case of a solution extraction, a minimum pH of about 13.5 of the basic solution is maintained throughout the extraction process, or, in the case of a resin treatment, an equivalent basicity is maintained.

The volume of the basic phase can be determined by practical limitations, such as reactor size and separation capacity, by the pH limits, and by molar equivalent ratios of base to acidic impurities. For instance, in the case of an extraction using aqueous NaOH, the volume of the basic first phase can, for example, be between one-tenth and one-third of the product second phase volume. The amount of NaOH or polymer-bound tetraorgano-ammonium hydroxide can, for example, be between about 0.05 and about 1 equivalent of the total amount of phosphorus in the triorganophosphite solution phase.

The contact time is, at least in part, a function of scale, mixing equipment, and hydrolysis rates of a specific organo-phosphite under conditions of basic extraction, and can, for example, be from about 15 minutes to about 5 hours.

For many processes using a basic additive, one or two extractions using a 10-fold excess of base to acid at a pH greater than 13 for about 15 to about 30 minutes should be sufficient. In the case of a treatment with a strongly basic anion-exchange resin comprising polymer-bound tetraorgano-ammonium hydroxide groups, the phase containing the phosphorus compounds can be mixed with a predetermined amount of the resin or the foresaid phase can be passed through a column containing the resin. The amount of resin used is, at least in part, a function of the amount of acidic impurities to be removed. For example, when using a strongly basic anion-exchange resin, a one time treatment with an amount of resin equivalent to a 6-10 fold excess of base to acid may be sufficient. The resin may be regenerated using a basic aqueous solution of NaOH as known by those skilled in the art.

Typically, the extraction process is relatively insensitive to pressure and, in this regard, is usually limited only by practical considerations. For practical reasons, preferred reaction pressure ranges can, for example, be from about 10 psia (69 kPa) to about 50 psia (345 kPa).

In the case of a liquid-liquid extraction, the basic solution may contain a soluble salt, such as NaCl, to aid the separation process.

To avoid further triorganophosphite hydrolysis, contact with the basic additive should ideally be done soon after the production of the crude phosphite mixture and preferably before further concentration and or heat exposure of the crude phosphite product mixture.

Acidic compounds to be removed may include, but are not restricted to, diorganohydrogenphosphite ($R^2$O)($R^3$O)POH, organodihydrogenphosphite ($R^1$O)(HO)PO(H), $H_3PO_3$, aromatic alcohols, and ammoniumhydrochlorides and ammoniumhydrobromides.

EXAMPLES

The following non-limiting examples further illustrate embodiments of the present invention.

Examples of the invention were prepared from crude phosphite mixtures containing one or more components having the following chemical structures: diorganohydrogenphosphite 5, organodihydrogenphosphite 6, monodentate triorganophosphites 7 and 8, phosphorochloridite 1, phosphorodichloridite 4, biphenol 2, and bidentate triorganophosphite 3.

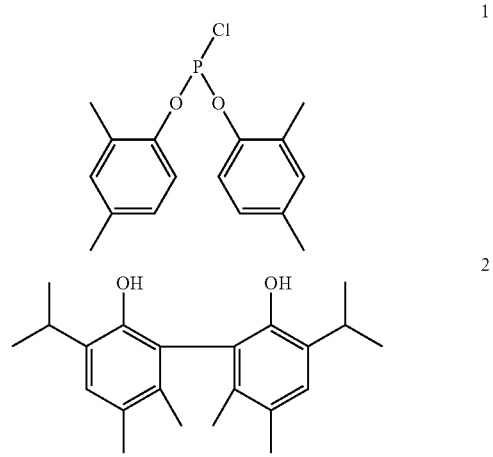

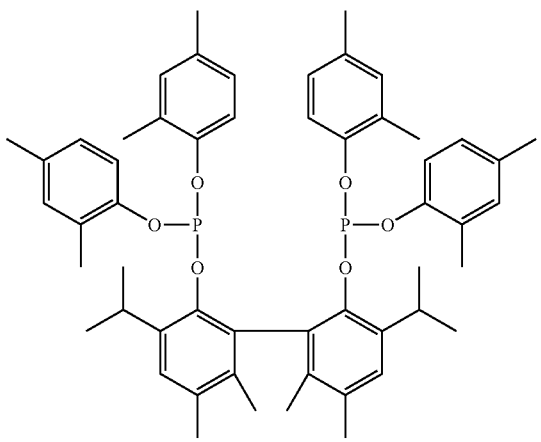

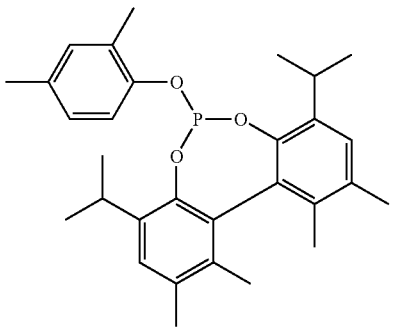

The following example shows that acidic diorganohydrogenphosphite 5, organodihydrogenphosphite 6, and H₃PO₃ representing primary hydrolysis products of triorganophosphites 7, phosphorochloridite 1, and phosphorodichloridite 4 can be significantly reduced or quantitatively removed from a solution containing the monodentate and bidentate triorganophosphites 7, 8, and 3 by extraction with an aqueous solution of a strong base. Results are summarized in Table 1 and reported graphically in FIG. 1. For quantitative NMR analysis, 0.250 mL of the organic phase and 0.600 mL of a 0.01 molar triphenylphosphine oxide (TPPO) in $C_6D_6$ were combined and analyzed by $^{31}P$ NMR (T1=5 sec.). Unless stated otherwise, the term brine refers to a saturated aqueous NaCl solution (about 26 wt % NaCl).

Example A

Synthesis of a Crude Phosphorochloridite 1 Containing Reaction Mixture

A temperature controlled 2000 mL baffled flask equipped with an overhead stirrer was charged with 400 mL of 1.0 molar $PCl_3$ in toluene and 4.0 mL 2.0 molar triethylamine in toluene. Under vigorous stirring, a solution of 411 mL 2.0 molar triethylamine in toluene and a solution of 411 mL 2.0 molar 2,4-xylenol in toluene were added separately and concurrently via peristaltic pump at 2.3 mL/min. During the addition period, the reaction temperature was maintained at 5° C. The $^{31}P$ NMR analysis exhibited transformation to the corresponding phosphorochloridite 1 ($^{31}P$ NMR chemical shift 162 ppm) in 90% selectivity. Other phosphorus containing components were triorganophosphite 7 (9%) and phosphorodichloridite 4 (1%) representing the crude solution of phosphorochloridite 1 used in the Water Extraction (Control Experiment) as well as Examples A1 and A2.

Water Extraction (Control Experiment):

Under nitrogen, 25 mL of the crude solution of phosphorochloridite 1 in toluene (0.56 molar) was combined with 14 mmol of triethylamine ($Et_3N$) and 10 mL of water ($H_2O$). The mixture was stirred vigorously for 5 minutes before the two phases were separated. $^{31}P$ NMR analysis of the organic phase indicated complete hydrolysis of phosphorochloridite 1 (162 ppm) to a mixture of the corresponding diorganohydrogenphosphite 5, organodihydrogenphosphite 6, and traces of $H_3PO_3$ ($^{31}P$ NMR chemical shifts −2 to +2 ppm). Subsequently, the organic phase was contacted with two successive portions of 10 mL 13 wt % brine and one portion of 10 mL 26 wt % brine by vigorous mixing for 5 minutes each, and subsequent separation of the two phases. Quantitative $^{31}P$ NMR analysis of the organic phase was conducted after each treatment with brine, but no significant reduction of hydrolysis products in the organic phase was observed at any time.

Example A1

Aqueous KOH Treatment

Under nitrogen, 25 mL of a 0.56 molar solution of phosphorochloridite 1 in toluene was combined with 14 mmol of $Et_3N$ and 10 mL of $H_2O$. The mixture was stirred vigorously for 5 minutes before the two phases were separated. $^{31}P$ NMR analysis of the organic phase indicated complete hydrolysis of phosphorochloridite 1 ($^{31}P$ NMR chemical shift 162 ppm) to a mixture of the corresponding diorganohydrogenphosphite 5, organodihydrogenphosphite 6, and traces of $H_3PO_3$ ($^{31}P$ NMR chemical shift −2 to +2 ppm). Subsequently, the organic phase was contacted with two successive portions of 10 mL 1 molar aqueous KOH and one portion of 10 mL 26 wt % brine by vigorous mixing for 5 minutes each, and subsequent separation of the two phases. Quantitative $^{31}P$ NMR analysis of the organic phase after each treatment with aqueous KOH was conducted indicating a significant reduction of hydrolysis products by the aqueous KOH treatment.

Example A2

Aqueous NaOH Treatment

Under nitrogen, 25 mL of a 0.56 molar solution of phosphorochloridite 1 in toluene were combined with 14 mmol of $Et_3N$ and 10 mL of $H_2O$. The mixture was stirred vigorously for 5 minutes before the two phases were separated. $^{31}P$ NMR analysis of the organic phase indicated complete hydrolysis of phosphorochloridite 1 to a mixture of the corresponding diorganohydrogenphosphite 5, organodihydrogenphosphite 6, and traces of $H_3PO_3$ ($^{31}P$ NMR chemical shift −2 to +2 ppm). Subsequently, the organic phase was contacted with two successive portions of 10 mL 1 molar aqueous NaOH and one portion of 10 mL 26 wt % brine by vigorous mixing for 5 minutes each, and subsequent separation of the two phases. Quantitative $^{31}P$ NMR analysis of the organic phase after each treatment was conducted indicating quantitative removal of hydrolysis products by the aqueous NaOH treatment.

TABLE 1

Fraction of Acidic Hydrolysis Products Diorganohydrogenphosphite 5, Organodihydrogenphosphite 6, and $H_3PO_3$ Remaining in the Organic Phase as Determined by $^{31}P$ NMR.

| Experiment | Step/Treatment | Remaining fraction of acidic hydrolysis products in organic phase (% mol) |
|---|---|---|
| Water Extraction (control) | 10 mL water, 8 mmol $Et_3N$ | 100% |
| | 10 mL 13 wt % brine | 99% |
| | 10 mL 13 wt % brine | 98% |
| | 10 mL 26 wt % brine | 100% |
| Example A1 | 10 mL water, 8 mmol $Et_3N$ | 100% |
| | 10 mL 1M KOH | 46% |
| | 10 mL 1M KOH | 7% |
| | 10 mL 26 wt % brine | 5% |
| Example A2 | 10 mL water, 8 mmol $Et_3N$ | 100% |
| | 10 mL 1M NaOH | 34% |
| | 10 mL 1M NaOH | 4% |
| | 10 mL 26 wt % brine | 0% |

FIG. 1 illustrates the results from Table 1 in graphical form.

The following Example and Table 2 show the benefit of strongly basic anion-exchange resin treatment for the purity and stability of the crude bidentate triorganophosphite 3 under exposure to water over an extended period of time, for example, under certain storage conditions.

Amberlyst™ A26-OH (Rohm and Haas Company) is a strong base, type 1, anionic, macroreticular polymeric resin based on crosslinked styrene divinylbenzene copolymer containing quaternary ammonium hydroxide groups; d=675 g/L, concentration of active sites=0.80 equiv/L.

Example B

Synthesis of a Crude Bidentate Triorganophosphite 3 Reaction Mixture

A temperature controlled 500 mL baffled flask equipped with an overhead stirrer was charged with 200 mL of 1.0 molar $PCl_3$ in toluene. Under vigorous stirring, a solution of 203.6 mL 2.0 molar triethylamine in toluene and a solution of 203.6 mL 2.0 molar 2,4-xylenol in toluene were added separately and concurrently via peristaltic pump at 2.9 mL/min. During the addition period, the reaction temperature was maintained at 5° C. The $^{31}P$ NMR analysis exhibited transformation to the corresponding phosphorochloridite 1 ($^{31}P$ NMR chemical shift 162 ppm) in 90% selectivity. Under vigorous stirring, 252.8 mmol of $Et_3N$ was added at 20° C., followed by a solution of 84.6 mL of 1.0 molar biphenol 2 via a peristaltic pump at 2 mL/min. The reaction mixture was vigorously contacted with 150 mL $H_2O$. Quantitative $^{31}P$ NMR analysis of the organic phase revealed a phosphorus distribution of 81 mol % bidentate triorganophosphite 3, 4 mol % monodentate triorganophosphite 8, 12 mol % monodentate triorganophosphite 7, and hydrolysis products 5, 6, and $H_3PO_3$ equaling 3 mol % of the total phosphorus content. This solution represents the crude bidentate triorganophosphite 3 reaction mixture used in the Brine Treatment (Control Experiment) and Example B1.

Brine Treatment (Control Experiment):

About 200 mL of the crude bidentate triorganophosphite 3 reaction mixture representing 67 mmol phosphorus was contacted with 50 mL of 26 wt % brine. Approximately 20% of the solvent was removed in vacuo at 40° C. over 30 minutes. The remaining solvent was removed in vacuo at 55° C. over one hour. Quantitative $^{31}P$ NMR analysis of the organic phase was conducted after the contact with brine, and of the concentrated sample, but no significant reduction of hydrolysis products in the organic phase was observed at any time.

The crude mixture was diluted with toluene to about 80 mL resulting in a 33 wt % mixture. To 40 mL of this mixture, representing about 34 mmol phosphorus, was added 0.4 mL of water and the mixture stirred vigorously for 6 days while monitoring the content of phosphorus compounds by $^{31}P$ NMR. Quantitative $^{31}P$ NMR analysis of the organic layer was conducted after 2 hours, 1 day, 2 days, 3 days, and 6 days. Results are summarized in Table 2 and indicate relatively fast hydrolysis of all the triorganophosphites.

Example B1

Resin Treatment

About 200 mL of the crude bidentate triorganophosphite 3 reaction mixture representing 67 mmol phosphorus was stirred with 11.5 g (13.6 mmol hydroxy anion equivalent) of Amberlyst™ A26-OH resin for two days. After the resin was removed, approximately 20% of the solvent was evaporated in vacuo at 40° C. over 30 minutes. The remaining solvent was removed in vacuo at 55° C. over one hour. Quantitative $^{31}P$ NMR analysis of the organic layer was conducted after treating with resin for two hours and two days. The results summarized in Table 2 indicate that all hydrolysis products were removed quantitatively after 2 hours of treatment, and no hydrolysis of the triorganophosphites was observed after prolonged treatment with resin over 2 days.

The crude mixture was diluted with toluene to about 80 mL resulting in a 33 wt % mixture. To 40 mL of this mixture, representing about 34 mmol phosphorus, was added 0.4 mL of water and the mixture stirred vigorously for 13 days. Quantitative $^{31}$P NMR analysis of the organic layer was conducted after 2 hours, 1 day, 2 days, 3 days, 6 days and 13 days. In contrast to the control experiment without Amberlyst™ A26-OH resin treatment, no significant increase in hydrolysis products was observed at any time.

TABLE 2

Fraction of Acidic Hydrolysis Products Diorganohydrogenphosphite 5, Organodihydrogenphosphite 6, and H$_3$PO$_3$ Compared to Bidentate Triorganophosphite 3 Remaining in the Organic Phase as Determined by $^{31}$P NMR.

| Experiment | Step/Treatment | Acidic hydrolysis Products (mol % Phosphorus) | Bidentate Triorganophosphite 3 (mol % Phosphorus) |
|---|---|---|---|
| Brine Experiment (control) | H$_2$O wash | 3 | 81 |
| | Brine treatment | 3 | 81 |
| | After concentrating | 3 | 81 |
| | 2 hours with H$_2$O | 4 | 81 |
| | 1 day with H$_2$O | 5 | 80 |
| | 2 days with H$_2$O | 11 | 75 |
| | 3 days with H$_2$O | 64 | 16 |
| | 6 days with H$_2$O | 66 | 15 |
| Example B1 | H$_2$O wash | 3 | 81 |
| | Resin 2 hours | 0 | 84 |
| | Resin 2 days | 0 | 84 |
| | 2 hours with H$_2$O | 0 | 85 |
| | 1 day with H$_2$O | 0 | 85 |
| | 2 days with H$_2$O | 0 | 85 |
| | 3 days with H$_2$O | 0 | 85 |
| | 6 days with H$_2$O | 0 | 85 |
| | 13 days with H$_2$O | 0 | 85 |

ADDITIONAL EXAMPLES

The following Examples demonstrate the removal of 3 mol % of total phosphorus and 6 mol % of total phosphorus, respectively, of acidic hydrolysis products diorganohydrogenphosphite 5, organodihydrogenphosphite 6, and H$_3$PO$_3$ by treatment with aqueous NaOH during the workup of a crude bidentate triorganophosphite 3.

Example 1

Synthesis of a Crude Bidentate Triorganophosphite 3 Reaction Mixture

A temperature controlled 2000 mL baffled flask equipped with an overhead stirrer was charged with 400 mL of 1.0 molar PCl$_3$ in toluene and 4.0 mL 2.0 molar triethylamine in toluene. Under vigorous stirring, a solution of 411 mL 2.0 molar triethylamine in toluene and a solution of 411 mL 2.0 molar 2,4-xylenol in toluene were added separately and concurrently via a peristaltic pump at 2.3 mL/min. During the addition period, the reaction temperature was maintained at 5° C. The $^{31}$P NMR analysis exhibited transformation to the corresponding phosphorochloridite 1 ($^{31}$P NMR chemical shift 162 ppm) in 90% selectivity. Under vigorous stirring, 600 mmol of Et$_3$N were added at 20° C. followed by a solution of 87.9 mL of 1.0 molar biphenol 2 via a peristaltic pump at a rate of 1.2 mL/min.

Workup:

After the completion of reaction, the reaction mixture was contacted with 300 mL of 13 wt % brine under vigorous stirring to remove triethylamine hydrochloride salts. Quantitative $^{31}$P NMR of the organic phase (Table 3) indicated hydrolysis products ($^{31}$P NMR chemical shift −2 to +2 ppm), equivalent to 3 mol % of the total phosphorus content. After separating, the organic phase was contacted with 300 mL of 20 wt % brine containing 8 mmol of NaOH (pH 12) followed by 300 mL of 26 wt % brine. Quantitative $^{31}$P NMR analysis of the organic phase indicated hydrolysis products equivalent to 3 mol % of total phosphorus ($^{31}$P NMR chemical shift −2 to +2 ppm) indicating that the amount of base used was not sufficient to remove the acidic impurities. Subsequently, the organic phase was contacted successively with 300 mL of 1 molar NaOH (pH 14) and 300 mL 26 wt % brine. Quantitative $^{31}$P NMR analysis of the organic phase indicated quantitative removal of the hydrolysis products. The molar distribution of phosphorus in the organic phase was 82% bidentate triorganophosphite 3 and 18% monodentate triorganophosphites 7 and 8 at $^{31}$P NMR chemical shifts of 133, 132, and 136 ppm, respectively.

TABLE 3

Phosphorus Distribution During Aqueous Workup with NaOH (Example 1)

| Step/Treatment | Acidic Hydrolysis Products (mol % Phosphorus) | Bidentate Triorganophosphite 3 (mol % Phosphorus) |
|---|---|---|
| 13% wt. brine | 3 | 78 |
| 20% wt. Brine + 8 mmol NaOH followed by 26% wt. brine | 2 | 79 |
| 1M NaOH followed by 26% wt. brine | 0 | 82 |

Example 2

Synthesis of a Crude Bidentate Triorganophosphite 3 Reaction Mixture

A temperature controlled 500 mL baffled flask equipped with an overhead stirrer was charged with 100 mL of 1.0 molar PCl$_3$ in toluene and 1.0 mL 2.0 molar triethylamine in toluene. Under vigorous stirring, a solution of 100 mL 2.0 molar triethylamine in toluene and a solution of 100 mL 2.0 molar 2,4-xylenol in toluene were added separately and concurrently via a peristaltic pump at 2.9 mL/min. During the addition period, the reaction temperature was maintained at 45° C. The $^{31}$P NMR analysis exhibited transformation to the corresponding phosphorochloridite 1 ($^{31}$P NMR chemical shift 162 ppm) in 89% selectivity. Under vigorous stirring, 130 mmol of Et$_3$N was added at 20° C. followed by a solution of 37.5 mL of 1.0 molar biphenol 2 via a peristaltic pump at 2 mL/min.

Workup:

The reaction mixture was vigorously contacted with 75 mL H$_2$O. Quantitative $^{31}$P NMR analysis of the organic phase indicated hydrolysis products equaling 6 mol % of the total phosphorus content (Table 4). After separating the aqueous phase, the organic phase was contacted successively with two portions of 75 mL 1 molar aqueous NaOH followed by 75 mL of 26 wt % brine. Quantitative $^{31}$P NMR analysis of the organic phase indicated quantitative removal of hydrolysis products. The molar distribution of phosphorus in the organic phase was 76% bidentate triorganophosphite 3 and 23% monodentate triorganophosphites 7 and 8 at $^{31}$P NMR chemical shifts of 133, 132, and 136 ppm, respectively.

TABLE 4

Phosphorus Distribution During Aqueous Workup with NaOH (Example 2)

| Step/Treatment | Acidic Hydrolysis Products (mol % Phosphorus) | Bidentate Triorganophosphite 3 (mol % Phosphorus) |
|---|---|---|
| H$_2$O | 6 | 71 |
| 1$^{st}$ 1M NaOH | 4 | 74 |
| 2$^{nd}$ 1M NaOH | 0 | 76 |

Many modifications and other embodiments of the inventions set forth herein will come to mind to one skilled in the art to which these inventions pertain having the benefit of the teachings presented in the foregoing descriptions and the associated FIGURE. Therefore, it is to be understood that the inventions are not to be limited to the specific embodiments disclosed and that modifications and other embodiments are intended to be included within the scope of the appended claims.

What is claimed is:

1. A method for preparing triorganophosphites, said method comprising:

a) contacting an alcohol with PCl$_3$ in the presence of a triorganoamine to produce a first reaction product comprising one or more organophosphites and triorganoamine hydrochloride;

b) removing the triorganoamine hydrochloride from the first reaction product to produce a second reaction product optionally containing one or more triorganophosphites, diorganohydrogenphosphite (R$^2$O)(R$^3$O)POH, organodihydrogenphosphite (R$^1$O)(HO)PO(H) and H$_3$PO$_3$, wherein R$^1$, R$^2$ and R$^3$ are independently selected from the group consisting of C$_1$ to C$_{18}$ alkyl, C$_6$ to C$_{18}$ aryl and hydroxyaryl, and C$_3$ to C$_{18}$ cycloalkyl and hydroxyalkyl radicals, and wherein R$^2$ and R$^3$ can optionally be connected to each other directly by a chemical bond or through an intermediate divalent group R$^9$, wherein R$^9$ is selected from the group consisting of —O—, —S—, and —CH(R$^{12}$)—, wherein R$^{12}$ is selected from the group consisting of H, C$_6$ to C$_{18}$ aryl, and C$_1$ to C$_{18}$ alkyl; and c) removing at least a portion of one or more of the compounds diorganohydrogenphosphite (R$^2$O)(R$^3$O)POH, organodihydrogenphosphite (R$^1$O)(HO)PO(H) and H$_3$PO$_3$ by contacting the second reaction product with a basic additive.

2. The method of claim 1, wherein the basic additive comprises at least one compound selected from the group consisting of NaOH, KOH, Na$_2$CO$_3$, K$_2$CO$_3$, Ca(OH)$_2$, NH$_4$OH, CaCO$_3$, a basic ion-exchange resin, and combinations thereof.

3. The method of claim 1, wherein step c) is repeated.

* * * * *